United States Patent
Horton, III et al.

(12)
(10) Patent No.: US 6,737,020 B1
(45) Date of Patent: *May 18, 2004

(54) MICROORGANISM NEUTRALIZATION DEVICE AND METHOD

(75) Inventors: Isaac B. Horton, III, Raleigh, NC (US); Kurt Anthony Garrett, Raleigh, NC (US)

(73) Assignee: Remotelight, Inc., Raleigh, NC (US)

( * ) Notice: Subject to any disclaimer, the term of this patent is extended or adjusted under 35 U.S.C. 154(b) by 102 days.

This patent is subject to a terminal disclaimer.

(21) Appl. No.: 09/723,731

(22) Filed: Nov. 28, 2000

(51) Int. Cl.[7] ................................................. A61L 2/00
(52) U.S. Cl. ..................... 422/24; 210/748; 250/455.11
(58) Field of Search ....................... 422/24; 250/450.11; 210/748

(56) References Cited

U.S. PATENT DOCUMENTS

| | | | |
|---|---|---|---|
| 5,780,860 A | 7/1998 | Gadgil et al. | |
| 5,992,684 A | 11/1999 | Russell | |
| 6,027,766 A | 2/2000 | Greenberg et al. | |
| 6,090,296 A | 7/2000 | Oster | |
| 6,094,767 A | 8/2000 | Iimura | |
| 6,103,363 A | 8/2000 | Boire et al. | |
| 6,110,528 A | 8/2000 | Kimura et al. | |
| 6,117,337 A | 9/2000 | Gonzalez-Martin et al. | |
| 6,403,030 B1 * | 6/2002 | Horton, III | 210/748 |
| 6,447,720 B1 * | 9/2002 | Horton et al. | 210/748 |
| 6,447,721 B1 * | 9/2002 | Horton et al. | 210/748 |
| 6,454,937 B1 * | 9/2002 | Horton et al. | 210/192 |

* cited by examiner

*Primary Examiner*—Krisanne Thornton
(74) *Attorney, Agent, or Firm*—Glasgow Law Firm, PLLC

(57) ABSTRACT

A processing method for treating organics-containing fluids including a ultraviolet (UV) disinfection step and a biological processing step. The UV light source employed in the UV disinfection step is positioned outside the fluid to be disinfected and the fluid is disinfected via exposure to at least one UV dose zone outside the fluid being treated wherein UV light is projected into the at least one dose zone. The UV light source may be presented in a vertical riser configuration, wherein the UV light source is positioned above the fluid to be treated and projecting a UV dose zone downward toward and into the fluid to be treated, with the fluid moving upward toward the UV light source. At least one interface plate is used to provide a surface zone for UV disinfection above the fluid and to provide additional treatment means for balancing pH, affecting effluent chemistry, reducing organic chemicals, and the like. Alternatively, the UV light source may be presented in a planar or horizontal design, wherein the UV light source is positioned above the fluid to be treated and projecting a UV dose zone downward toward and into the fluid to be treated, with the fluid moving in a direction substantially perpendicular to the UV dose zone. After neutralization, the fluid is directed to the biological processing step, wherein microbes or enzymes are contacted with the fluid to effect metabolism of the organics in the fluid. The process may be used to reduce the organic load of animal and non-animal wastes, as well as produce a desired product from microbial foodstocks or enzyme substrates.

74 Claims, 4 Drawing Sheets

MICROORGANISM NEUTRALIZATION DEVICE AND METHOD

BACKGROUND OF THE INVENTION (1) Field of the Invention

This invention relates generally to ultraviolet (UV) sterilization of fluids and fluid-based mixtures and, more particularly, to a microorganism neutralization UV device and method.

(2) Description of the Prior Art

Wastewater Discharge Problems and Regulatory Standards

The rapid expansion of intensive-confinement animal rearing facilities has created the secondary problem of excessive organic waste being discharged into the environment. Excessive organic waste, if not properly treated and disposed, can cause several problems, including the changing of aerobic environments to anaerobic ones with resulting suffocation and demise of aerobic species, the proliferation and spreading of human and animal pathogens, and the fouling of air with noxious microbial anaerobic metabolic byproducts. In recognition of this problem of excessive organic waste discharge, US governmental agencies have imposed restrictions on the quality and quantity of waste discharged by a point source.

Bacterial Fermentative Processes

Waste solutions containing high organic material can be treated to reduce the quantity of organic material by allowing the waste to undergo bacterial fermentation for a period of time. The fermentation can be performed under aerobic or anaerobic conditions. Generally, aerobic fermentation is the most prevalent method, as it does not require the specialized equipment and containers necessary to maintain the anaerobic state required by anaerobic fermentation. Aerobic fermentation is accomplished by simply pumping atmospheric air through the waste solution in the presence of aerobic fermentative bacteria. By contrast, anaerobic fermentation requires specialized containment vessels to prevent contact of the solution with air, and additionally requires a more elevated temperature than aerobic fermentation in order to maintain the metabolism of the anaerobic bacteria at a sufficient level to make the process efficient. However, anaerobic fermentation has recently found more application, due to the fact that this process generates methane gas, which is an energy source, as a by-product.

Fermentative processes of complex organic solutions generally rely on several species of bacteria working in synergy to effectively consume the available organic molecules for their growth. Because several species of bacteria are required to effect the degradation of the myriad of organic products found in biological waste solutions, and especially animal waste solutions, the lack of one or more of these species in the solution can severely delay or prevent the complete degradation of the organic products. Therefore, to prevent such delays, these microbes are often added to the waste solutions at or near the start of fermentation in order to act as an aid to fermnentation. These bacterial cultures were designed to ensure that no essential component of the fermentative microbial flora was deficient, and therefore that adequate fermentation would be accomplished within a normal time period. Unfortunately, several problems existed with such a treatment method and bacterial fermentation in general. First, such systems do not always give consistent performance despite the addition of microbial fermentative culture because the indigenous microbial flora may effectively out-compete the desirable fermentative bacteria, resulting in a slow and/or incomplete degradation of the waste solution and overgrowth of potential pathogens. Second, a breakdown in the supply of air or oxygen would slow the metabolism of the aerobic fermentative bacteria, with the resulting problem of slow and/or incomplete degradation of the organic waste. Finally, uncontrolled fermentation may allow the indiscriminate overgrowth of human, animal, and plant pathogens, creating an animal and/or human health hazard if discharged into the environment. In the latter case, antimicrobial feed additives retained in the waste could inhibit growth of beneficial fermentative bacteria, with the resultant overgrowth of any antibiotic-resistant endogenous flora. This situation could be potentially dangerous, should these endogenous flora be human or animal pathogens.

Thus, there remains a need for a method that is more reliable and effective in reducing the organic matter of waste solutions. Another pressing need is to reduce the number of potentially pathogenic microbes discharged in bacterially-treated waste.

Biofilter

Another method to effect the fermentative degradation of organic waste is through the use of a biofilter. A biofilter is essentially a fixed support that provides surface area for the fermentative bacteria to adhere to. The waste fluid is then directed over the support containing the microbes, at which time the microbes uptake nutrients from the passing fluid. By retaining the bacteria on a fixed surface, they are exposed to a sufficient amount of organic waste to support their metabolism. This system is generally used with dilute waste streams that would be too difficult to treat with a standard aerobic or anaerobic digester system, since nutrient availability to the bacteria in these systems is limited by the diffusion rate of the nutrients through the water. While this system can reduce the organic content of dilute waste, it cannot reduce the levels of pathogenic bacteria already contained in the waste.

Thus, there remains a need for a method that is more reliable and effective in reducing the number of potentially pathogenic microbes discharged into wetland-based treatment systems.

Modified Constructed Wetland

A more recently developed organic waste-handling method is one in which the waste stream is allowed to run into an appropriately constructed wetland. In the wetland, microscopic organisms, including aerobic and anaerobic bacteria, degrade the organic waste. In addition, protozoa, plants, and large animals, including birds, are allowed to thrive in the wetland as a means of absorbing the nitrogen and other inorganic nutrient inputs to the wetland. Unfortunately, because such a treatment system allows the contact of raw animal waste with vectors such as migratory birds, the potential exists for the spread of human and animal pathogens well beyond the immediate vicinity of the waste treatment facility.

Thus, there remains a need for a method that is more reliable and effective in reducing the number of potentially pathogenic microbes discharged into wetland-based treatment systems.

In summary, there remains a need for a wastewater treatment method that is more reliable and effective in reducing the organic matter of waste solutions and can also reduce the number of potentially pathogenic microbes discharged in bacterially-treated waste.

SUMMARY OF THE INVENTION

The present invention is directed to an organic fluid treatment method, whereby an organic fluid is pretreated by UV disinfection and then additionally treated with reactive components to effect a change in the constitution of the fluid. In the preferred embodiment, the organic fluid is directed through a UV disinfection device, then treated with microorganisms to effect the degradation of the organics in the fluid. Preferably, the UV disinfection device is a vertical riser configuration.

The present invention is further directed to a method for treating animal waste, whereby the animal waste is directed through a UV disinfection device, then treated with microorganisms to effect the degradation of the animal waste. Preferably, the UV disinfection device is a vertical riser configuration.

The present invention is further directed to a method for treating non-animal waste, whereby the non-animal waste is directed through a UV disinfection device, then treated with reactive components to effect the degradation of the non-animal waste.

The present invention is further directed to a method for manufacturing a product from a microorganism-containing fluid, whereby the microorganism-containing fluid is directed through a UV disinfection device, then treated with reactive components to produce the desired product.

Accordingly, one aspect of the present invention is to provide an ultraviolet disinfection (UV) system for treating organic waste-containing fluid, the system comprising at least one light source positioned within a housing and connected to a power source for producing a UV light output from the housing, the system including at least one optical component positioned between the at least one light source and the UV light output from the housing, thereby producing a focused, controllable UV light output that has at least one UV dose zone for providing effective sterilization of microorganisms within the water.

Another aspect of the present invention is to provide a method for purifying organic waste-containing fluid comprising the steps of providing the fluid to be treated in a reservoir; diluting the fluid; exposing the reservoir and fluid to a UV system including at least one light source positioned within a housing and connected to a power source for producing a UV light output from the housing, the system including at least one optical component positioned between the at least one light source and the UV light output from the housing; producing a focused, controllable UV light output that has at least one UV dose zone for providing effective neutralizing of microorganisms within the fluid; and adding reacting components, including microorganisms for breakdown of organic waste within the fluid.

These and other aspects of the present invention will become apparent to those skilled in the art after a reading of the following description of the preferred embodiment when considered with the drawings.

DETAILED DESCRIPTION OF THE PREFERRED EMBODIMENTS

Figure 1:
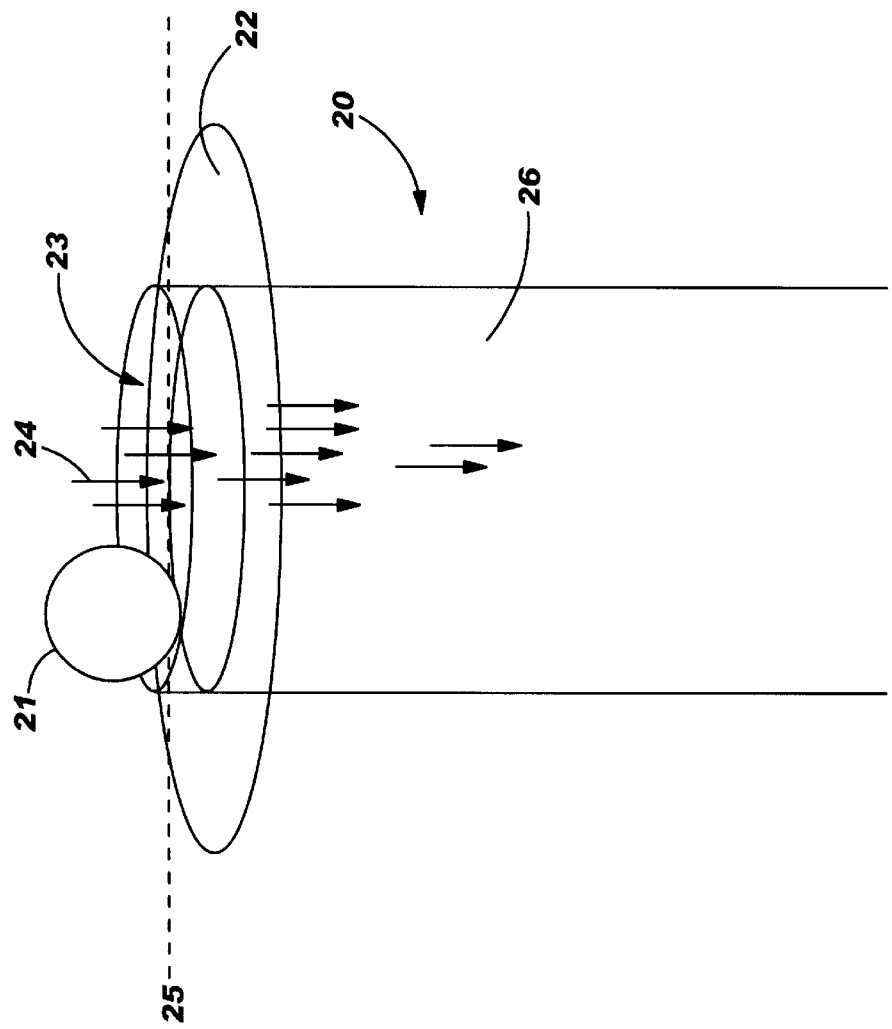
FIG. 1 is an illustration of a side view of a UV disinfection system constructed according to the present invention in a vertical riser configuration.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Referring now to the drawings in general, the illustrations are for the purpose of describing a preferred embodiment of the invention and are not intended to limit the invention thereto. As best seen in FIG. 1, a preferred embodiment is shown according to the present invention; in contrast and clear distinction to the prior art, the UV light source according to the present invention is not submerged in the fluid to be disinfected.

The present invention is directed to an ultraviolet (UV) disinfection system and method for treating for treating fluids including a configuration and design to function effectively with at least one UV light source or lamp that is not submerged in the fluid. The UV light source may be presented in a vertical riser configuration, as shown generally at 20 in FIG. 1, wherein the at least one UV light source is positioned above the fluid to be treated and projecting UV light rays 24 downward toward and into the fluid to be treated, with the fluid moving upward toward the UV light source. These UV light rays may be projected downward from a UV light source or a lamp system (not shown) including optical components (not shown). These optical components are positioned between the UV light source or lamp and the output, thereby focusing, directing, and controlling the light rays that are exposed to the fluid and that sterilize any microorganisms 21 (significantly enlarged) that exist in the fluid. Several UV dose zones are established within the system. The first zone is the air UV dose zone 25 which occurs just beneath the UV light source and just above the water and the at least one interface plate 23. The next zone is the interface plate UV dose zone 22 which occurs at the intersection of the water and the at least one interface plate. The at least one interface plate is used to provide a surface zone for UV disinfection above the fluid and to provide additional treatment means for balancing pH, affecting effluent chemistry, providing a catalyst, and the like. The last zone is the submerged UV dose zone 26, which creates a variable UV dose zone that decreases in effectiveness at greater distances from the UV light source.

Figure 2:
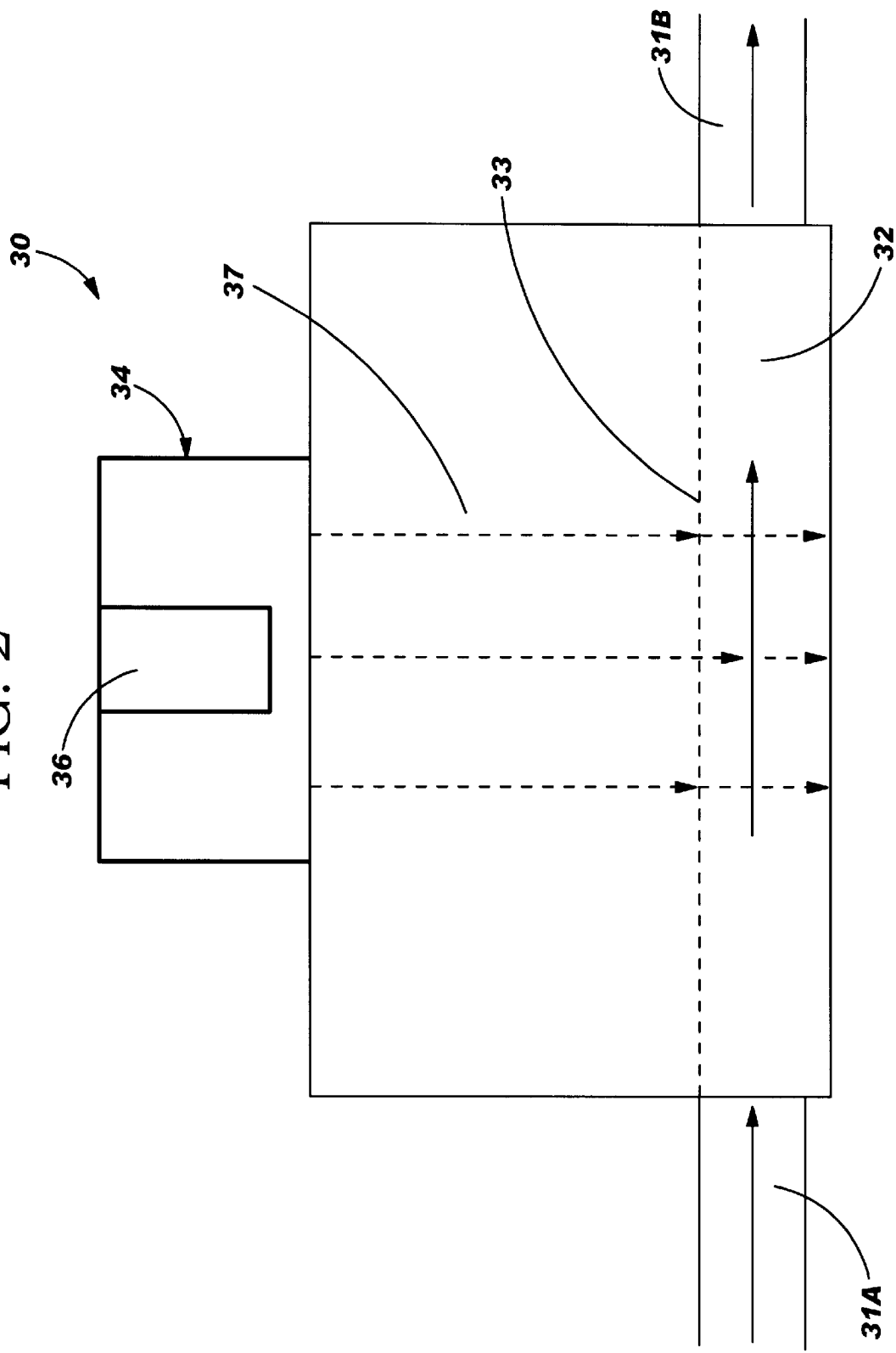
FIG. 2 is an illustration of a side view of an alternative embodiment of the present invention.

Alternatively to the vertical configuration, the UV light source may be presented in a planar or horizontal design, as shown generally at 30 in FIG. 2, wherein the UV light source 36 is positioned within a UV light source system 34, including optical components (not shown), above the fluid to be treated and projecting a UV dose zone downward toward and into the fluid to be treated, with the fluid moving from the influent point 31A in a direction substantially perpendicular to the UV light source toward the effluent point 31B. Several UV dose zones are established within the system. The first zone is the air UV dose zone 37 which occurs just beneath the UV light source and just above the water. The next zone is the air/water interface UV dose zone 33 which occurs at the air and water interface. The last zone is the submerged UV dose zone 32, which occurs within the flowing water.

Figure 3:
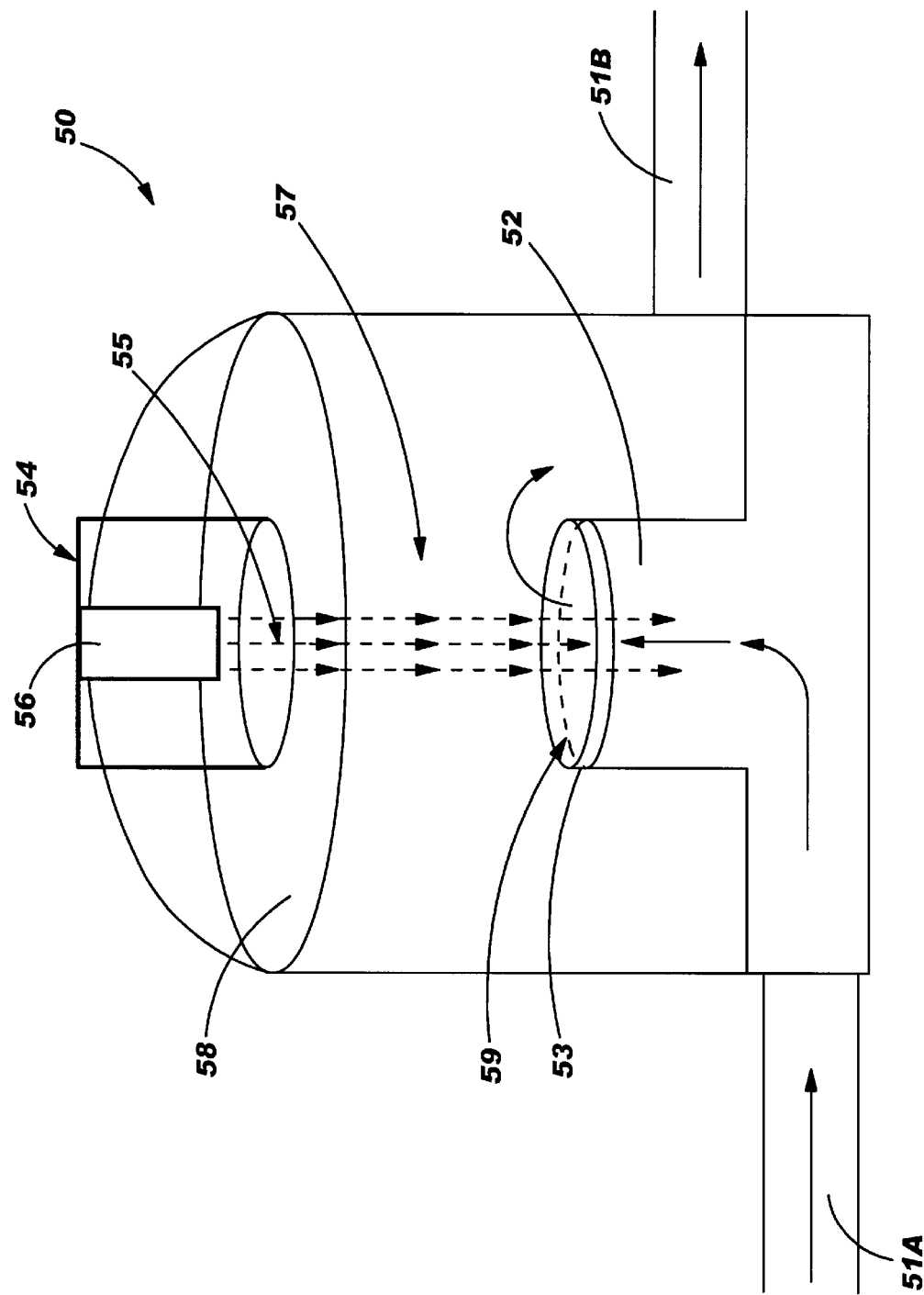
FIG. 3 is an illustration of a side view of an alternative embodiment of the present invention in a single column vertical riser configuration.

The present invention allows a significantly simplified system, potentially significantly lower operating costs, and the capacity to process large quantities of water as well as relatively small quantities, as for personal or in-home use. For an in-home system, as best illustrated in FIG. 3, a single vertical riser UV light source system, shown generally at 50, is constructed and configured to be attached to a water storage unit sized for a dwelling. In this system, the UV light source 56 is positioned within a UV light source system 54, including optical components (not shown), above the fluid to be treated and projecting a UV dose zone downward toward and into the fluid to be treated, with the fluid moving from the influent point 51A, flowing vertically toward the UV light source, and then exits the effluent point 51B. The at least one UV light source is positioned above the fluid to be treated and projecting UV light rays 55 downward toward and into the fluid to be treated, with the fluid moving upward toward the UV light source. Several UV dose zones are established within the system. The first zone is the light source system exit UV dose zone 58 which occurs at the light source system and air interface. Then next zone is the air UV dose zone 57 which occurs just beneath the UV light source and just above the water and the at least one interface plate 59. The next zone is the interface plate UV dose zone 53 which occurs at the intersection of the water and the at least one interface plate. The at least one interface plate is used to provide a surface zone for UV disinfection above the fluid and to provide additional treatment means for balancing pH, affecting effluent chemistry, providing a catalyst, and the like. The last zone is the submerged UV dose zone 52, which creates a variable UV dose zone that decreases in effectiveness at greater distances from the UV light source.

Figure 4:
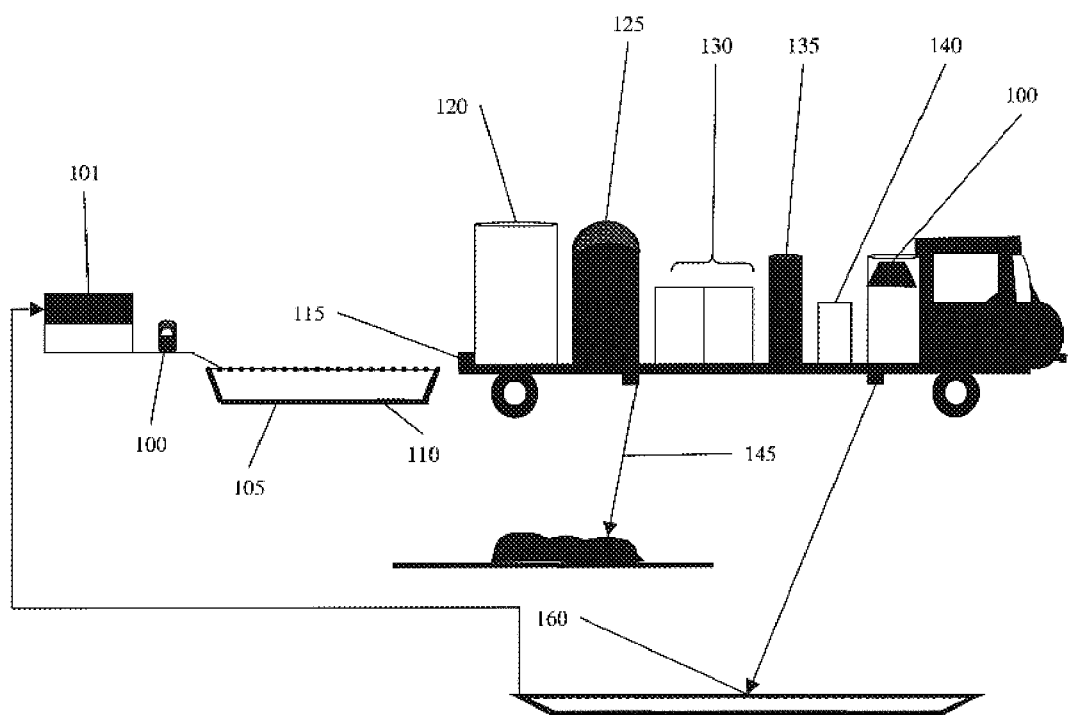
FIG. 4 is an illustration of an alternative embodiment of a system according to the present invention.

FIG. 4 illustrates an alternative embodiment of a system according to the present invention. Shown in FIG. 4 is a UV Reactor 100, which treats animal waste coming from an animal confinement facility 101, thereby reducing or eliminating ammonia formation and encouraging methane formation. The waste is directed toward a UV equipped holding pond 105, where the waste is stored. UV doses are administered to the waste during storage to eliminate microorganisms and encourage methane production. The waste storage may also include a lined and covered anaerobic digester 110, to favor the generation of methane. Periodic pick-up 115 of the waste occurs, wherein a mobile waste treatment facility arrives and pumps the waste through a treatment system, the first stage of which is a separator unit 120, where chemical flocculants can be injected, if needed. Next the waste is directed to a vertical clarifier 125, which removes heavy solids. Electronic flocculation can be performed here to remove salts. Next, the waste is directed to a series of filters 130, using sand followed by diatomaceous earth. Next, the waste is routed to an activated carbon filter with regenerator 135, then to bag type polishing filters 140 that include 1 micron cartridge to fine eliminate carbon dust. Finally, the waste water is routed through a UV Reactor 100 to sterilize the purified water, which is finally pumped to a lined and covered pond 160 for water storage and reuse as flush, irrigation, and animal drinking. During the process, heavy solids are captured and removed for re-use 145, such as for methane production for power generation, and high octane alcohol.

The preferred embodiment of the organic fluid treatment system incorporates the steps of turbidity control, UV disinfection, and biological processing. Turbidity control is important, as high turbidity will decrease the UV penetration and consequently reduce the sterilization efficiency of the system. Traditional means for reducing turbidity, including, but not limited to, filtration, dilution, reverse osmosis and chemical treatment, may be advantageously employed to increase the UV efficacy of the system according to the present invention. Alternately, new methods, such as electromagnetic force separation, may be used.

After turbidity control, the fluid is directed to the UV disinfection system for sterilization. After sterilization, the fluid is directed to the biological processor, where the fluid contacts and is acted upon by microbes or enzymes.

The organic fluid may be derived from animal or non-animal waste, or may be a microbial foodstock. The process may be one that reduces the organic load of these fluids and/or produces a desirable product. After biological processing, the fluid may be re-directed to a UV disinfection system in order to re-sterilize the fluid.

The UV disinfection system may be a vertical riser configuration system (VRC). In the vertical riser configuration the UV light source is positioned above the waste-containing fluid to be treated and projecting a UV dose zone downward toward and into the waste-containing fluid to be treated, with the waste-containing fluid moving upward toward the UV light source. The non-submerged configuration of the present invention prevents the problems associated with extreme temperatures in the fluid. Fluorescent lamps, including UV lamps, lose a significant amount of output at low termperatures. Thus, a non-submerged system, which separates the lamp from the fluid to be treated, allows for the temperature of the lamp to be maintained at more optimal temperature, without necessitating cooling or heating the fluid as well. Thus, this system more efficiently disinfects extreme environments, such as freezers, coolers, hot water heaters, and the like.

Alternatively, the UV light source may be presented in a planar or horizontal design, wherein the UV light source is positioned above the waste-containing fluid to be treated and projecting a UV dose zone downward toward and into the waste-containing fluid to be treated, with the waste-containing fluid moving in a direction substantially perpendicular to the UV dose zone.

Several UV dose zones are established within the VRC system. The first zone is the light source system exit UV dose zone, which occurs at the light source system and air interface. Then next zone is the air UV dose zone, which occurs just beneath the WV light source and just above the water and the at least one interface plate. The next zone is the vapor zone, which occurs just above the water surface. The next zone is the interface plate UV dose zone, which occurs at the intersection of the water and the at least one interface plate. The last zone is the submerged WV dose zone, which creates a variable UV dose zone that decreases in effectiveness at greater distances from the UV light source.

The VRC system may include quick-connect lamps and housings with a monitoring and indicator system that would indicate that a lamp had failed. Each riser may have an individual, dedicated lamp and optical system with overlap between neighboring lamps to eliminate dead zone. Each riser in the VRC system may also have a valve that shuts of the riser in case of failure.

In the VRC system, the interface zone may be formed by incorporation of an interface plate that possesses catalytic properties such that certain reactions are catalyzed in the vicinity of the interface plate. For example, $TiO_2$ may be incorporated into the interface plate that is made of glass or other appropriate material. When such a plate is irradiated with UV light, fatty acids and other organic chemicals are chemically reduced, resulting in degradation to smaller volatile products such as methane, ethane, etc. Additionally, nitrate ion is reduced to elemental nitrogen in such a system.

Additionally, UV light can catalyze a variety of reactions, and the use of UV light with any one or combination of the plethora of available chemical catalyst generates numerous possible catalytic combinations that are used to catalyze a myriad of desirable reactions. The photocatalyst may include photo-activated semiconductors such as Titanium Oxide; TiO2 (photo activation wavelength; not more than 388 nm), Tungsten Oxide; WO2 (photo activation wavelength; not more than 388 nm), Zinc Oxide; ZnO (photo activation wavelength; not more than 388 nm), Zinc Sulfide; ZnS (photo activation wavelength; not more than 344 nm) and Tin Oxide; SnO2 (photo activation wavelength; not more than 326 nm). In addition to these catalysts, other catalysts, such as $PtTiO_2$, are known. TiO2 may be preferably applied as the photocatalyst, considering that the activation power is very high, the catalyst is long-lived with high durability, and safety for human applications is certified, as TiO2 has been used safely for a long time in cosmetic and food applications. Additionally, the interface plate may be a biofilter, and contain enzymes or bacteria that react with substrates contained in the fluid.

The interface plate may also perform mechanical or other physical functions. For example, the plate may grind and/or sift particles contained within the fluid. The plate may also provide cooling, heat, steam, or gas(es) to the reaction zone to enhance desired reactions or inhibit undesired reactions. Heat, steam, or other gases may also be added in order to increase the vapor zone. In addition, the interface plate may induce turbulence or cause fluid cascade with a non-planar surface, stair-step surface, downwardly sloping surface, or other the like. In general, the interface plate can be used to facilitate surface reactions and/or surface/air reactions. While generally regarding the UV light source and configuration thereof, the preferred embodiment of the present invention includes at least one optical component positioned between the UV light source and the UV light source system output point. Advantageously, the use of optical components enables the system to maximize the intensity, focus, and control of the UV light rays at the output for any given UV light source or lamp. Also, optical components, including but not limited to reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920, which are commonly owned by the assignee of the present invention, and which are incorporated herein by reference in their entirety. Additionally, optical component such as gratings, splitting reflectors, dichroic filters, focalizers, gradient lenses and reflectors, and off-axis lenses and reflectors may be used.

With regard to lenses, several embodiments are envisioned. Imaging lenses, such as a parabolic lens, and non-imaging lenses, such as gradient lenses, may be used. A gradient lens collects light through a collecting opening and focuses it to an area smaller than the area of the collecting opening. This concentration is accomplished by changing the index of refraction of the lens along the axis of light transmission in a continuous or semi-continuous fashion, such that the light is "funneled" to the focus area by refraction. An example of gradient lens technology is the Gradium® Lens manufactured by Solaria Corporation. Alternatively, a toroidal reflector, as described in U.S. Pat. No. 5,836,667, is used. In this embodiment, a UV radiation source, such as an arc lamp, is located at a point displaced from the optical axis of a concave toroidal reflecting surface. The concave primary reflector focuses the radiation from the source at an off-axis image point that is displaced from the optical axis. The use of a toroidal reflecting surface enhances the collection efficiency into a small target, such as an optical fiber, relative to a spherical reflecting surface by substantially reducing aberrations caused by the off-axis geometry. A second concave reflector is placed opposite to the first reflector to enhance further the total flux collected by a small target.

Additionally, more than one reflector may be used with a lamp. For example, dual reflectors or three or more reflectors, as taught in U.S. Pat. Nos. 5,706,376 and 5,862,277, may be incorporated into the preferred embodiment.

In general, the transmissive optical components are UV transmissive and the reflective optical components are UV reflective. Any of the optical components, including the housing, may be made of acrylic or similar materials that degrade over time when exposed to UV light. In particular, the fiber optic components may be composed of acrylic, glass, liquid core, hollow core, core-sheath, or a combination. These components can be replaced when their performance has deteriorated to an unacceptable level.

Notably, any number of lamps including low pressure, medium pressure, high pressure, and ultra high-pressure lamps, which are made of various materials, e.g., most commonly mercury (Hg), can be used with the system configuration according to the present invention, depending upon the fluid or influent characteristics and flow rates through the system. Furthermore, while high and ultra high pressure lamps have not been used commercially to date by any prior art system, predominantly because of the low energy efficiency associated with them and the lack of capacity for prior art design and configuration formulas to include high pressure UV lamps, the present invention is advantageously suited to accommodate medium to high to ultra high pressure lamps. In particular, a preferred embodiment according to the present invention employs medium to high-pressure UV lamps, more preferably high-pressure UV lamps. The present invention is advantageously suited to accommodate medium to high to ultra high pressure lamps, all of which can be metal, halogen, or a combination metal halide. Additionally, spectral calibration lamps, electrodeless lamps, and the like can be used.

In particular, a preferred embodiment according to the present invention employs a pencil-type spectral calibration lamp. These lamps are compact and offer narrow, intense emissions. Their average intensity is constant and reproducible. They have a longer life relative to other high wattage lamps. Hg (Ar) lamps of this type are generally insensitive to temperature and require only a two-minute warm-up for the mercury vapor to dominate the discharge, then 30 minutes for complete stabilization.

A Hg (Ar) UV lamp, which is presently commercially available and supplied by ORIEL Instruments, is used in the preferred embodiment according to the present invention. The ORIEL Hg(Ar) lamp, model 6035, emits UV radiation at 254 nm. When operated at 15 mA using a DC power supply, this lamp emits 74 microwatt/cm2 of 254 nm radiation at 25 cm from the source.

The system according to the present invention uses medium to high pressure UV lamps configured and functioning above the fluid or water flow, not immersed in the fluid flow as with all prior art systems designed for use in all water treatment applications. With this system, the number of lamps necessary to treat a given influent and flow rate can be reduced by perhaps a factor of ten, which is a major advantage in practical application. Also, the lamps are not susceptible to fouling, since they are not immersed in the fluid to be disinfected. Additionally, the design of the present invention allows for a significant reduction in heat in the water. Furthermore, the maintenance and servicing is greatly simplified. Also, in the vertical riser configuration according to one preferred embodiment configuration, the reactor design, which would comprise a number of cylindrical tubes oriented vertically, includes a hydraulic system having pumping equipment and a significant amount of pumping power. Furthermore, the present invention is an optical UV light source system for use in a waste-containing fluid disinfection system. As such, traditional mathematical models used for determining energy efficiencies for the present invention are inadequate and inapplicable. Thus, given the use of optical components associated with the UV light source, the use of medium to ultra high pressure UV lamps, and the introduction of at least one UV dose zone existing outside the water to be treated, the present system presents a revolutionary approach for designing, constructing, and operating a UV waste-containing fluid disinfection system that is nowhere taught or suggested in the prior art or mathematical models for predicting waste-containing fluid disinfection and flow rates thereof.

The present invention allows a significantly simplified system, potentially significantly lower operating costs, and the capacity to process large quantities of fluid as well as relatively small quantities.

The following section sets forth selected particular design examples for particular wastewater processing applications.

DESIGN EXAMPLES

This section outlines a few design examples, not necessarily perfected or optimized, but illustrative of what can be done for a UV fluid disinfection system and method, wherein the fluid is wastewater. These design examples include: Swine waste aerobic digester system, swine waste anaerobic digester system, swine waste upflow biofilter system, and swine waste modified wetlands treatment system.

In this preferred embodiment, swine waste is flushed through a bar screen of the appropriate dimensions to remove large, solid materials. Waste passing through the bar screen is then directed to a grit chamber. The waste is allow sufficient residence time in the grit chamber to allow dense particles to sediment to the bottom. Supernatant from the grit chamber is then pumped through a dilution device that reduces the turbidity of the waste through the addition of clarified water from the clarifier basin. A turbidity meter positioned upstream from the clarified water injection port controls the waste dilution. After injection of the dilution water, the diluted solution is mixed to ensure sufficient homogeneity, and then directed through a UV sterilization system.

The UV sterilization system in these examples is a vertical riser system, as described in U.S. patent application Ser. No. 09/630245, which is incorporated herein by reference in its entirety. The UV sterilization system as described utilizes medium-pressure, high-pressure, and very high-pressure lamps to achieve high intensity UV light in the UV dose zones.

After sterilization, the diluted wastewater is directed to the aerobic digester. In the digester, sufficient air is injected into the wastewater to maintain adequate metabolism of the fermentative bacteria. Additional fermentative bacteria can be added to the incoming wastewater to aid fermentation. Enhanced fermentation means the residence time of the waste in the digester can be reduced, with a commensurate reduction in the size of the digester required. After sufficient digestion of the organic waste is effected in the digester, the treated effluent from the digester may be re-directed through a UV-sterilization step, if necessary, as outlined above. This sterilization step may be performed by the same device used in the pre-treatment sterilization or may be performed by another device dedicated to the sterilization of the post-digestion waste stream. The waste stream may then be directed to a clarifier basin, if necessary. This basin allows any biosolids not digested and/or generated in the digester to sediment for collection. The clarified supernatant from the clarifier basin can then be routed to a holding pond, re-used to flush the swine facilities, used in the dilution of the wastewater in the dilution device, and/or mixed with the UV-treated wastewater entering the digester in order to provide fermentative bacteria.

Swine Waste Anaerobic Digester System

In this alternative preferred embodiment, swine waste is flushed through a bar screen of the appropriate dimensions to remove large, solid materials. Waste passing through the bar screen is then directed to a grit chamber. The waste is allow sufficient residence time in the grit chamber to allow dense particle to sediment to the bottom. Supernatant from the grit chamber is then pumped through a dilution device that reduces the turbidity of the waste through the addition of clarified water from the clarifier basin. A turbidity meter positioned upstream from the clarified water injection port controls the waste dilution. After injection of the dilution water, the diluted solution is mixed to ensure sufficient homogeneity, and then directed through the UV sterilization system. After sterilization, the diluted wastewater is directed to the anaerobic digester. In the digester, the wastewater is heated to a temperature sufficient to maintain adequate metabolism of the fermentative bacteria. Additional fermentative bacteria can be added to the incoming wastewater to aid fermentation. Enhanced fermentation means the residence time of the waste in the digester can be reduced, with a commensurate reduction in the size of the digester required. After sufficient digestion of the organic waste is effected in the digester, the treated effluent from the digester may be re-directed through a UV-sterilization step, if necessary, as outlined above. This sterilization step may be performed by the same device used in the pre-treatment sterilization or may be performed by another device dedicated to the sterilization of the post-digestion waste stream. The waste stream may then be directed to a clarifier basin, if necessary. This basin allows any biosolids not digested and/or generated in the digester to sediment for collection. The clarified supernatant from the clarifier basin can then be routed to a holding pond, re-used to flush the swine facilities, used in the dilution of the wastewater in the dilution device, and/or mixed with the UV-treated wastewater entering the digester in order to provide fermentative bacteria.

Swine Waste Biofilter Digester System

In this alternative preferred embodiment, swine waste is flushed through a bar screen of the appropriate dimensions to remove large, solid materials. Waste passing through the bar screen is then directed to a grit chamber. The waste is allow sufficient residence time in the grit chamber to allow dense particle to sediment to the bottom. Supernatant from the grit chamber is then pumped through a dilution device that reduces the turbidity of the waste through the addition of clarified water from the clarifier basin. A turbidity meter positioned upstream from the clarified water injection port controls the waste dilution. After injection of the dilution water, the diluted solution is mixed to ensure sufficient homogeneity, and then directed through the UV sterilization system. After sterilization, the diluted wastewater is directed to the biofilter digester. In the biofilter, the wastewater is directed over supports covered with fermentative bacteria that absorb organic waste from the wastewater. These supports can be composed of material that is fixed to the interior of the biofilter chamber or material that remains suspended in the interior of the biofilter and is of sufficient density to not be carried away by the flowing wastewater. The wastewater is heated to a temperature sufficient to enhance the metabolism of the fermentative bacteria. Additional fermentative bacteria can be added to the incoming wastewater to reseed the biofilter and enhance fermentation. Enhanced fermentation allows for reduction of the residence time of the waste in the digester, with a commensurate reduction in the digester size required. After passing through the biofilter, the treated effluent from the biofilter may be re-directed through a UV-sterilization step, if necessary, as outlined above. This sterilization step may be performed by the same device used in the pre-treatment sterilization or may be performed by another device dedicated to the sterilization of the post-biofilter waste stream. The waste stream may then be directed to a clarifier basin, if necessary. This basin allows any biosolids not digested and/or generated in the biofilter to sediment for collection. The clarified supernatant from the clarifier basin can then be routed to a holding pond, re-used to flush the swine facilities, used in the dilution of the wastewater in the dilution device, and/or mixed with the UV-treated wastewater entering the digester in order to provide fermentative bacteria to the biofilter.

Swine Waste Modified Wetlands Area

In this alternative preferred embodiment, swine waste is flushed through a bar screen of the appropriate dimensions to remove large, solid materials. Wastewater passing through the bar screen is then directed to a grit chamber. The wastewater is allowed sufficient residence time in the grit chamber to allow dense particle to sediment to the bottom. Supernatant from the grit chamber is then pumped through a dilution device that reduces the turbidity of the waste through the addition of clarified water from the clarifier basin. A turbidity meter positioned upstream from the clarified water injection port controls the waste dilution. After injection of the dilution water, the diluted solution is mixed to ensure sufficient homogeneity, and then directed through the UV sterilization system. After sterilization, the diluted wastewater is directed to the modified wetland area. After sufficient digestion of the organic waste is effected in the wetlands, the treated effluent from the wetlands may be re-directed through a UV-sterilization step, if necessary, as outlined above. This sterilization step may be performed by the same device used in the pre-treatment sterilization or may be performed by another device dedicated to the sterilization tof the post-digestion waste stream. The waste stream may then be directed to a clarifier basin, if necessary. The clarified supernatant from the clarifier basin can then be routed to a holding pond, re-used to flush the swine facilities, used in the dilution of the wastewater in the dilution device, and/or mixed with the UV-treated wastewater entering the wetlands area in order to provide fermentative bacteria to the influent area of the wetlands.

While the alternative preferred embodiments set forth in the foregoing are described independently, it is within the scope of this invention to include these alternative preferred embodiments separately or in combination, depending on the specific requirements of a given influent or waste to be treated and the output requirements.

In addition to enhancing the efficiency of the waste treatment systems, pre-sterilization eliminates potential pathogens in the waste and allows for a more well-characterized microbial population in the output, as shown in Table 1, below.

TABLE 1

Levels of pathogen elimination and output microbial characterization in preferred embodiments and prior art systems.

| System | Pathogen elimination | Output microbial characterization |
|---|---|---|
| Prior art aerobic digester | 2 | 2 |
| Prior art anaerobic digester | 1 | 1 |
| Prior art biofilter | 1 | 1 |
| Prior art wetlands | 1 | 1 |
| Preferred embodiment aerobic digester | 5 | 4 |
| Preferred embodiment anaerobic digester | 5 | 4 |
| Preferred embodiment biofilter | 5 | 5 |
| Preferred embodiment wetlands | 5 | 3 |

1-Very Low  2-Low  3-Some  4-High  5-Very High

Certain modifications and improvements will occur to those skilled in the art upon a reading of the foregoing description. By way of example, various optical components are used depending upon the particular UV light source or lamp selection for a given system. Also, a plurality of UV light source systems, either planar horizontal or retrofit configurations and/or cylindrical vertical riser configurations, may be combined and arranged in series to increase the flow rates for which effective UV disinfection of the fluid occurs. Moreover, a wide range of fluid applications, including application of the organic fluid disinfection method to wastewater, commercial and industrial wastewater, agricultural sludge and other waste and wastewater, biomedical and bodily fluids, fluid contaminants influents, and effluents, microbial foodstocks, enzymatic substrates, and the like for the purpose of reduction of organic wastes or production of desired product are contemplated applications for the present invention, without substantial departure from the embodiments and teachings contained within this specification. All modifications and improvements have been deleted herein for the sake of conciseness and readability but are properly within the scope of the following claims.

We claim:

1. An ultraviolet disinfection (UV) system for treating organics-containing fluid, the system comprising at least one light source positioned within a housing and connected to a power source for producing a UV light output from the housing, the system including at least one optical component positioned between the at least one light source and the UV light output from the housing, thereby producing a focused, controllable UV light output that has at least one UV dose zone for providing effective sterilization of microorganisms within the fluid.

2. The UV system according to claim 1, wherein the at least one UV light source is one lamp.

3. The UV system according to claim 1, wherein the at least one UV light source is a UV lamp.

4. The UV system according to claim 3, wherein the at least one UV light source is a spectral calibration lamp.

5. The UV system according to claim 3, wherein the at least one UV light source is an electrodeless lamp.

6. The UV system according to claim 3, wherein the at least one UV light source is a mercury halide lamp.

7. The UV system according to claim 1, wherein the at least one UV light source is a light pump device.

8. The UV system according to claim 7, wherein the output from the at least one UV light source is distributed by fiber optic transmission lines.

9. The UV system according to claim 7 wherein the fiber optic transmission lines having a first end connected to the housing output such that the UV light output from the housing passes through the fiber optic transmission lines and exiting from a second end such that the UV light output exiting the fiber optic transmission lines is projected into the fluid.

10. The UV system according to claim 8, wherein the fiberoptic lines include acrylic fibers.

11. The UV system according to claim 8, wherein the fiberoptic lines include glass fibers.

12. The UV system according to claim 8, wherein the fiberoptic lines include liquid core fibers.

13. The UV system according to claim 8, wherein the fiberoptic lines include hollow core fibers.

14. The UV system according to claim 8, wherein the fiberoptic lines include core-sheath fibers.

15. The UV system according to claim 8, wherein at least one fluid-containing device is connected to the light pump device via fiberoptic transmission lines.

16. The UV system according to claim 1, further including a non-fouling lamp housing thereby eliminating cleaning of the lamp housing to ensure consistent UV disinfection of the fluid.

17. The UV system according to claim 1, wherein the light housing is affixed to a reservoir and the UV light output disinfects a substantially non-flowing fluid supply contained within the reservoir.

18. The UV system according to claim 17, wherein the system has a non-vertical riser configuration.

19. The UV system according to claim 1, wherein the lamp housing is affixed to a reservoir with flowing fluid contained therein.

20. The UV system according to claim 2, further including a vertical riser configuration (VRC) wherein the fluid is moved at a predetermined rate toward the UV light output thereby producing an increasing UV dose within the fluid as it approaches the light output.

21. The UV system according to claim 20, wherein the interface zone further includes at least one additive that influence characteristics of the fluid as the fluid passes through the interface zone and over the surface zone.

22. The UV system according to claim 21, wherein the additives is selected from the group consisting of TiO2, WO2, ZnO, ZnS, SnO2, and $PtTiO_2$ and the like.

23. The UV system according to claim 20, wherein the vertical riser configuration system is portable.

24. The UV system according to claim 20, wherein the vertical riser configuration system is scalable to applications.

25. The UV system according to claim 20, wherein the system is adaptable to be removably connected to a piping system for carrying fluid to an end user output, such that a multiplicity of systems may be positioned to function at a corresponding multiplicity of end user outputs to provide disinfected, purified fluid in many locations at once.

26. The UV system according to claim 1, wherein the at least one optical component is selected from the group consisting of reflectors, shutters, lenses, splitters, focalizers, mirrors, rigid and flexible light guides, homogenizer, mixing rods, manifolds and other couplers, filters, gratings, diffracters, color wheels and fiber optic transmission lines.

27. The UV system according to claim 1, wherein at least one optical component is an off-axis optical component.

28. The UV system according to claim 1, wherein at least one optical component is a gradient component.

29. The UV system according to claim 1, wherein at least one optical component is UV transmissive.

30. The UV system according to claim 1, wherein at least one optical component is UV reflective.

31. The UV system according to claim 26 wherein the at least one optical component includes fiber optic transmission lines having a first end connected to the housing output such that the UV light output from the housing passes through the fiber optic transmission lines and exiting from a second end such that the UV light output exiting the fiber optic transmission lines is projected into the fluid.

32. The UV system according to claim 26, wherein the at least one optical component is a lens for focusing light from the light source through an output point in the housing and into the fluid for disinfection thereof.

33. The UV system according to claim 26, wherein the at least one optical component is a parabolic lens.

34. The UV system according to claim 1, wherein the at least one UV dose zone includes a fluid-air interface dose zone and a variable intra-fluid dose zone.

35. The UV system according to claim 1, wherein the at least one UV light source is positioned outside the fluid to be treated thereby providing effective sterilization of microorganisms within the fluid.

36. An ultraviolet disinfection (UV) system for treating organics-containing fluid, the system comprising at least one light source positioned outside the fluid to be treated and positioned within a housing and connected to a power source for producing a UV light output from the housing, the system including at least one optical component positioned between the at least one light source and the UV light output from the housing, thereby producing a focused, controllable UV light output that has at least one UV dose zone for providing effective sterilization of microorganisms within the organics-containing fluid.

37. The UV system according to claim 36, wherein the at least one UV light source is a single UV lamp.

38. The UV system according to claim 36, wherein the at least one UV light source is a spectral calibration lamp.

39. The UV system according to claim 36, wherein the at least one UV light source is an electrodeless lamp.

40. The UV system according to claim 36, wherein the at least one UV light source is a mercury halide lamp.

41. The UV system according to claim 36, wherein the at least one UV light source is a light pump device.

42. The UV system according to claim 36, further including a non-fouling lamp housing thereby eliminating cleaning of the lamp housing to ensure consistent UV disinfection of the fluid.

43. The UV system according to claim 36, wherein the light housing is affixed to a reservoir and the UV light output disinfects a substantially non-flowing fluid supply contained within the reservoir.

44. The UV system according to claim 43, wherein the system has a non-vertical riser configuration.

45. The UV system according to claim 36, wherein the lamp housing is affixed to a reservoir with flowing fluid contained therein.

46. The UV system according to claim 36, further including a vertical riser configuration (VRC) wherein the fluid is moved at a predetermined rate toward the UV light output thereby producing an increasing UV dose within the fluid as it approaches the light output.

47. The UV system according to claim 36, wherein the interface zone further includes at least one additive that influence characteristics of the fluid as the fluid passes through the interface zone and over the surface zone.

48. The UV system according to claim 47, wherein the additives is selected from the group consisting of TiO2, WO2, ZnO, ZnS, SnO2, and $PtTiO_2$ and the like.

49. The UV system according to claim 46, wherein the vertical riser configuration system is scalable to applications.

50. The UV system according to claim 46, wherein the system is adaptable to be removably connected to a piping system for carrying fluid to an end user output, such that a multiplicity of systems may be positioned to function at a corresponding multiplicity of end user outputs to provide disinfected, purified fluid in many locations at once.

51. The UV system according to claim 36, wherein the at least one optical component is selected from the group consisting of reflectors, shutters, lenses, splitters, focalizers, mirrors, rigid and flexible light guides, homogenizer or mixing rods, manifolds and other couplers, filters, gratings, diffracters, color wheels and fiber optic transmission lines.

52. The UV system according to claim 36, wherein at least one optical component is UV transmissive.

53. The UV system according to claim 36, wherein at least one optical component is UV reflective.

54. The UV system according to claim 36, wherein the at least one optical component includes fiber optic transmission lines having a first end connected to the housing output such that the UV light output from the housing passes through the fiber optic transmission lines and exiting from a second end such that the UV light output exiting the fiber optic transmission lines is projected into the fluid.

55. The UV system according to claim 54, wherein the fiberoptic lines include acrylic fibers.

56. The UV system according to claim 54, wherein the fiberoptic lines include glass fibers.

57. The UV system according to claim 54, wherein the fiberoptic lines include liquid core fibers.

58. The UV system according to claim 54, wherein the fiberoptic lines include hollow core fibers.

59. The UV system according to claim 54, wherein the fiberoptic lines include core-sheath fibers.

60. The UV system according to claim 51, wherein the at least one optical component is a lens for focusing light from the light source through an output point in the housing and into the fluid for disinfection thereof.

61. The UV system according to claim 60 wherein the lens is a parabolic lens.

62. The UV system according to claim 36, wherein the at least one UV dose zone includes a fluid-air interface dose zone and a variable intra-fluid dose zone.

63. A method for purifying organics-containing fluid comprising the steps of:
providing the fluid to be treated in a reservoir;
exposing the reservoir and fluid to a UV system including at least one light source positioned within a housing and connected to a power source for producing a UV light output from the housing, the system including at least one optical component positioned between the at least one light source and the UV light output from the housing;
producing a focused, controllable UV light output that has at least one UV dose zone for providing effective neutralizing of microorganisms within the fluid;
adding reacting components, including microorganisms for further processing of organics within the fluid.

64. The method according to claim 63 further including the steps of repeating all the steps until a desired level of purification is achieved.

65. The method according to claim 63, further including post-treatment of the fluid and solid waste extracted therefrom.

66. The method according to claim 63, wherein the system includes a non-submerged light source.

67. The method according to claim 63, wherein the at least one optical component is a UV-transmissive component.

68. The method according to claim 63, wherein the at least one optical component is a UV-reflective component.

69. A method for providing ultraviolet disinfection (UV) of organics-containing fluid, the method comprising the steps of:
pre-treating an organics-containing fluid to be neutralized, including biofiltration;
diluting the fluid;
providing a UV neutralization system comprising at least one UV light source outside a fluid to be neutralized and at least one interface zone positioned between the at least one UV light source and the fluid to be treated, the at least one UV light source designed, configured, and connected to produce UV light creating at least one UV dose zone outside the fluid;
presenting a surface zone on the at least one interface zone, wherein the surface zone has a UV dose zone associated therewith for disinfecting the fluid to be treated;
introducing a pre-treated fluid into the system, the fluid passing through at least one UV dose zone within the fluid and passing through the at least one interface zone and surface zone UV dose zone;
disinfecting the fluid via exposure to the UV light in the UV dose zones;
dispensing the neutralized fluid outside the system.

70. The method according to claim 69, further including the step of forcing the diluted fluid via a hydraulic system through a vertical riser configuration of the system.

71. The method according to claim 69, further including the step of modifying the fluid characteristics via at least one additive on the interface zone causing a reaction in the fluid.

72. The method according to claim 69, further including the step of mechanical sifting of the organics-containing fluid prior to dilution and neutralization.

73. The method according to claim 69, further including the step of introducing turbulence in the fluid as the fluid passes throughout the system, thereby increasing the exposure to UV light and disinfection thereby.

74. The method according to claim 69, further including the step of introducing a catalyst at the interface zone.

* * * * *